(12) United States Patent  (10) Patent No.: US 7,458,983 B2
Hamilton et al.  (45) Date of Patent: Dec. 2, 2008

(54) LASER IONIZATION THERAPY SYSTEM AND METHOD

(75) Inventors: J. Steve Hamilton, Littleton, CO (US); Scott Hamilton, Littleton, CO (US); Steve Hamilton, Littleton, CO (US)

(73) Assignee: Laser Cleanse, Littleton, CO (US)

( * ) Notice: Subject to any disclaimer, the term of this patent is extended or adjusted under 35 U.S.C. 154(b) by 121 days.

(21) Appl. No.: 11/150,482

(22) Filed: Jun. 13, 2005

(65) Prior Publication Data

US 2006/0015158 A1  Jan. 19, 2006

Related U.S. Application Data

(63) Continuation of application No. 10/366,459, filed on Feb. 14, 2003, now Pat. No. 6,913,616.

(51) Int. Cl.
*A61N 5/06* (2006.01)
(52) U.S. Cl. .................................................. 607/89
(58) Field of Classification Search .............. 607/88–94
See application file for complete search history.

(56) References Cited

U.S. PATENT DOCUMENTS

| 4,438,498 | A | * | 3/1984 | Sekel et al. | 702/60 |
| 4,696,721 | A | * | 9/1987 | Higashino et al. | 205/67 |
| 5,514,168 | A | * | 5/1996 | Friedman | 607/89 |
| 6,280,591 | B1 | * | 8/2001 | Akutsu et al. | 204/471 |
| 6,929,934 | B1 | * | 8/2005 | Korchev et al. | 435/173.1 |
| 2003/0034249 | A1 | * | 2/2003 | Akutsu et al. | 204/499 |
| 2003/0136205 | A1 | * | 7/2003 | Totoki | 73/864.71 |

OTHER PUBLICATIONS

Article "Ionization Therapy" originally published in Explore! For the professional, vol. 11, No. 4, 2002, staff writer.

* cited by examiner

*Primary Examiner*—Henry M Johnson, III
(74) *Attorney, Agent, or Firm*—McKenna Long & Aldridge LLP

(57) ABSTRACT

A detoxification method includes immersing at least a portion of a patient's body within a reservoir filled with water; generating ions within the water; and simultaneously with the generating ions, irradiating a predetermined area of the therapy subject with light generated by a cold laser. The generated light may be irradiated to the patient as either a continuous beam or a pulsed beam. The ions generated within the water may be positive, negative, or combinations thereof. Further, the light may be irradiated as long as the ions are being generated.

18 Claims, 8 Drawing Sheets

LASER IONIZATION THERAPY SYSTEM AND METHOD

This application is a continuation of U.S. patent application Ser. No. 10/366,459, filed Feb. 14, 2003, now U.S. Pat. No. 6,913,616, the contents of which are hereby incorporated by reference.

BACKGROUND OF THE INVENTION

1. Field of the Invention

The present invention relates to a laser ionization therapy system and method capable of efficiently removing toxins from a patient's body.

2. Discussion of the Related Art

Disease, stress, surgeries and other medical procedures, environmental toxins, cigarette smoking, alcohol consumption, improper nutrition, and other major and minor abuses tend to leave the human body weak and toxic. Because of poor diets and high stress, the body tends to accumulate and store excessive quantities of waste products such as diacetic, lactic, pyurvic, carbonic, acetic, butyric, and hepatic acids. Acids can attack joints, tissues, muscles, organs, and glands causing minor to major dysfunction. Many detoxification techniques and therapies include ascorbic acid flush, blood purification, chelation therapy, exercise, fasting, hyperbaric oxygen therapy, hydrotherapy, juicing, light therapy, acupuncture, acupressure, biofeedback, chiropractic therapy, herbal supplements, massage, meditation, etc., to detoxify, heal, or otherwise remove stress accumulated by the body. Accordingly, many therapies may be difficult, time consuming, unhealthy, and even painful.

Light therapy has a proven ability that is founded both in history and in science. As far back as 4000 BC, Rig Veda, the sacred books of India, describe the healing power of the Sun God Sanitar. Throughout the Middle Ages, red light was used to treat small pox where the sick were placed in a room illuminated by dim red light filtered through thick red curtains. The Danish physician and Nobel peace prize winner Niels Ryberg Finsen also employed red light to treat scarring that occurs with small pox. Further, several scientific theories have been proposed in attempts to explain basic physiological events occurring at a cellular level when laser irradiation is applied to the body. A bioluminescence theory recognizes that DNA replication emits light between 630 and 640 nm and, therefore, light by a He—Ne or ERCHONIA™ laser may accelerate DNA replication via photonic stimulation. Today, a type of light therapy called cold laser therapy, for example, uses a low intensity beam of laser light capable of stimulating natural healing processes at a cellular level. Cold laser therapy has proven effective in the area of chiropractic therapy in reducing pain and swelling, promoting healing processes, in treating old injuries, etc.

In addition to the aforementioned therapies, ionization therapy is currently being used to detoxify the body. Using ionization therapy, a power supply is connected to an electrode array. The electrode array is immersed within a tub of water along with the hands, feet, or whole body of the patient. Next, the power supply delivers a low voltage direct current into the electrode array to generate positively and negatively charged ions within the water. The generated ions travel through the body and neutralize oppositely charged particles which are then diffused out of the body through dispersion wherever the body contacts the water. Ionization therapy often detoxifies the whole body more effectively and faster than any herbal or fasting therapies and results in little or no stress to the patient.

However effective ionization therapy is, the body still is often not fully relaxed at the cellular level. Therefore, the efficiency with which related art ionization therapy apparatus detoxify the body is not optimized. It was this understanding and recognition of the problems with the related art ionization therapy systems that formed the impetus for the present invention.

SUMMARY OF THE INVENTION

Accordingly, the present invention is directed to a laser ionization therapy system that substantially obviates one or more of the problems due to limitations and disadvantages of the related art.

An advantage of the present invention aids in the detoxification of a human body.

Another advantage of the present invention provides enhanced detoxification techniques using existing equipment having previously been used in diverse therapeutic treatments.

Additional features and advantages of the invention will be set forth in the description which follows, and in part will be apparent from the description, or may be learned by practice of the invention. These and other advantages of the invention will be realized and attained by the structure particularly pointed out in the written description and claims hereof as well as the appended drawings.

To achieve these and other advantages and in accordance with the purpose of the present invention, as embodied and broadly described, a detoxification method may, for example, include contacting at least a portion of a therapy subject with water; generating ions within the water for a predetermined period of time; and irradiating the therapy subject with substantially coherent light during the predetermined period of time.

In another aspect of the present invention, a detoxification method may, for example, include immersing at least a portion of a patient's body within a reservoir filled with water; generating ions within the water; and simultaneously with the generating ions, irradiating a predetermined area of the therapy subject with laser light.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, examples of which are illustrated in the accompanying drawings.

Figure 1:
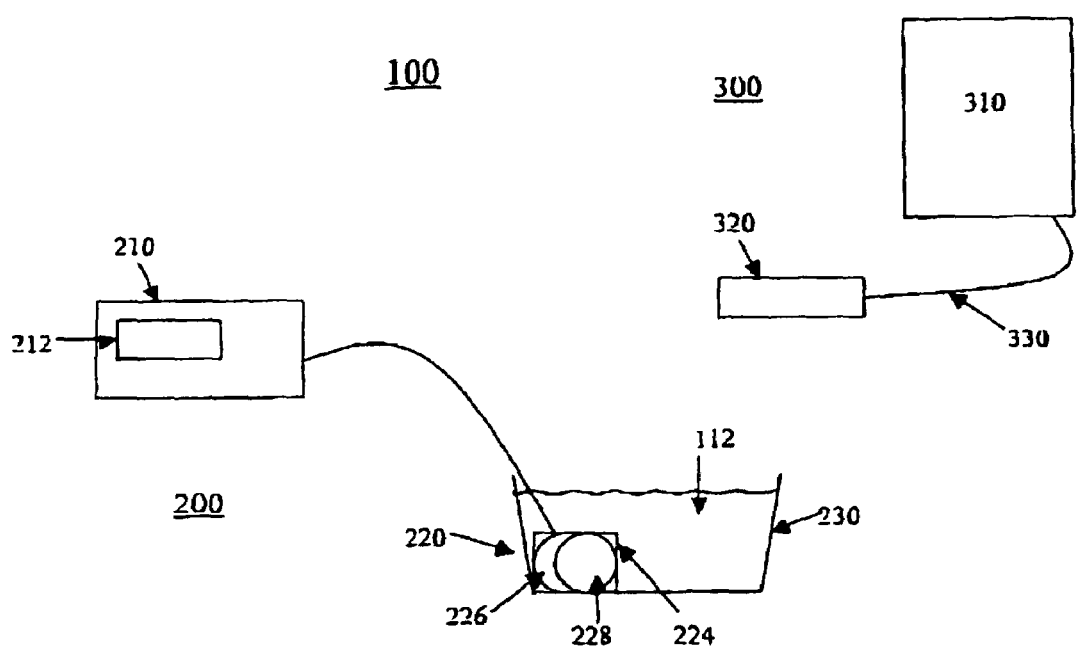
FIG. 1 illustrates the laser-ionization therapy system according to the principles of the present invention.
Figure 2A:
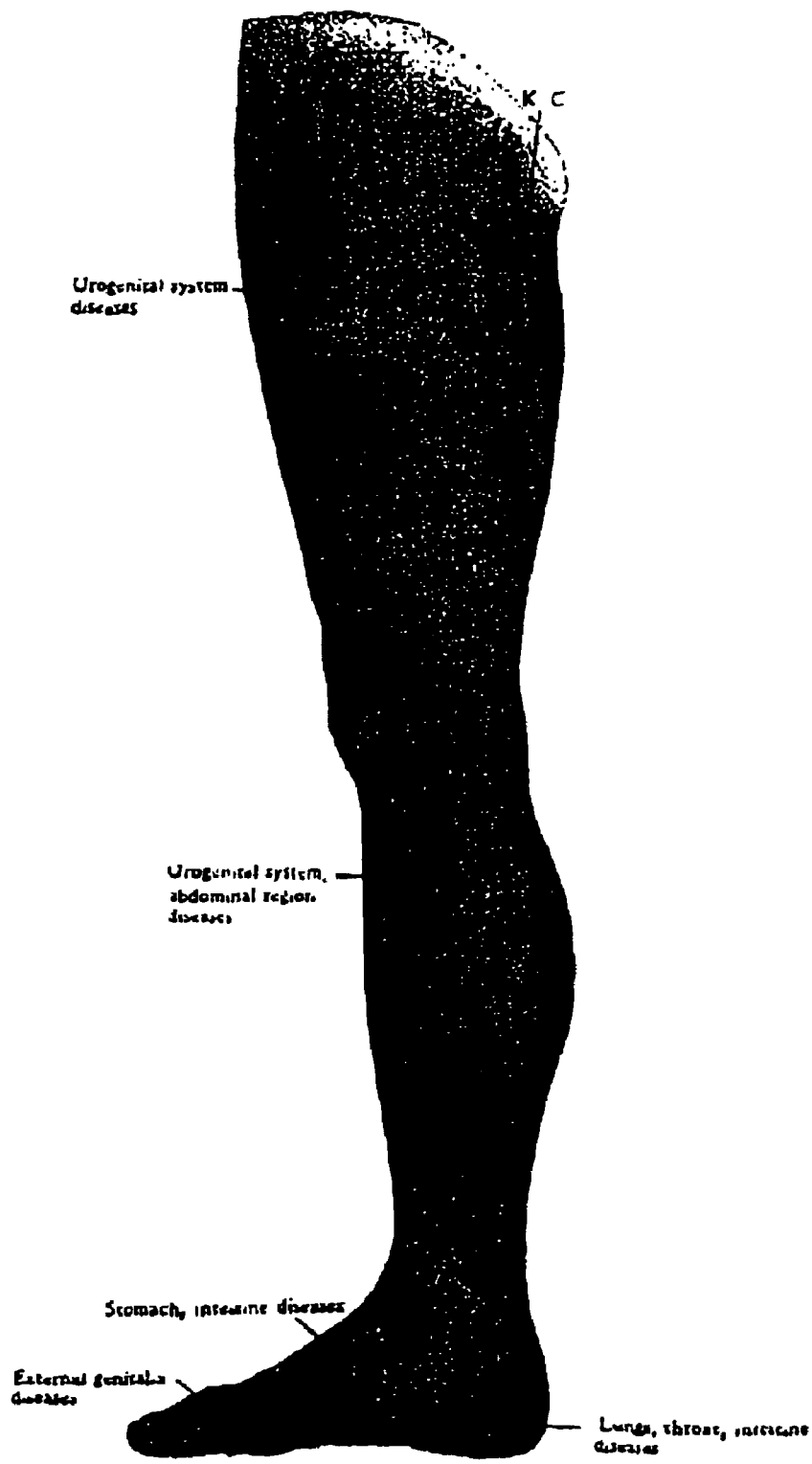
FIGS. 2A-G illustrate predetermined areas of a patient's body that may be irradiated with light.
Figure 2B:
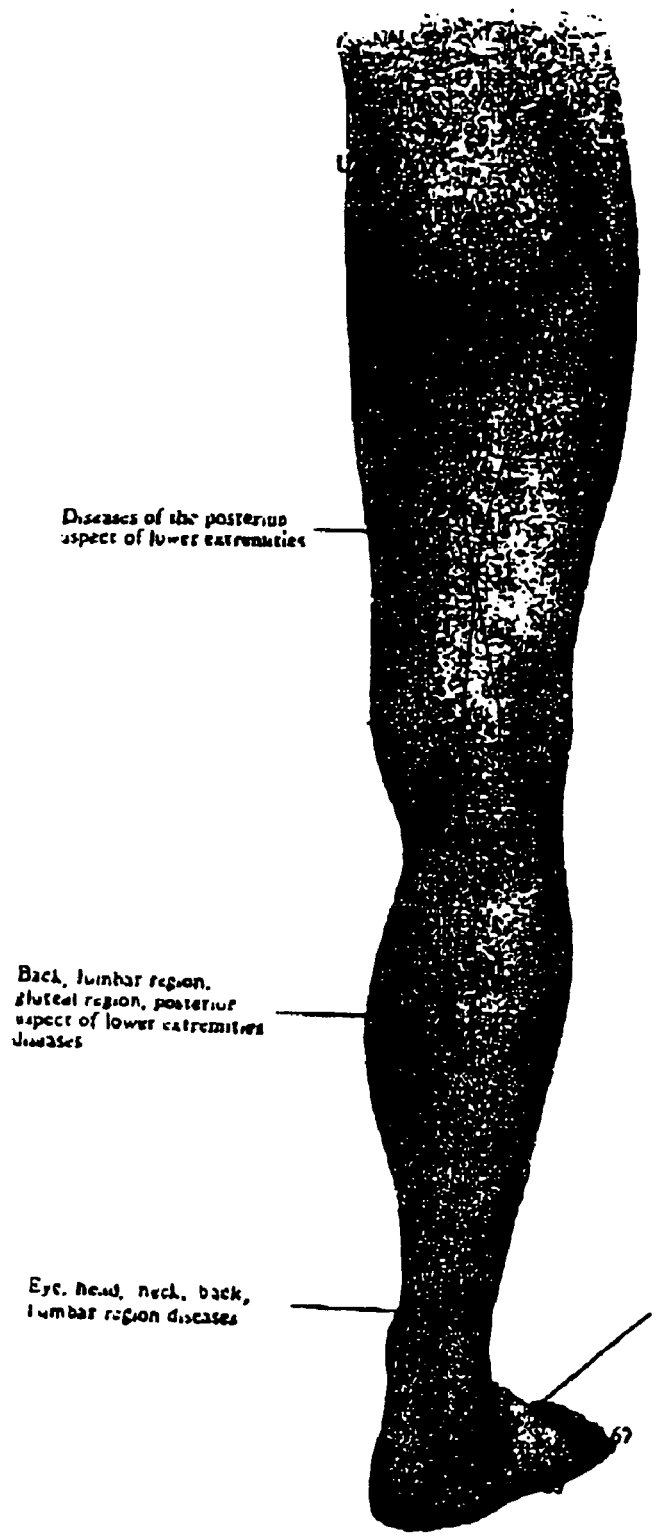
Figure 2C:
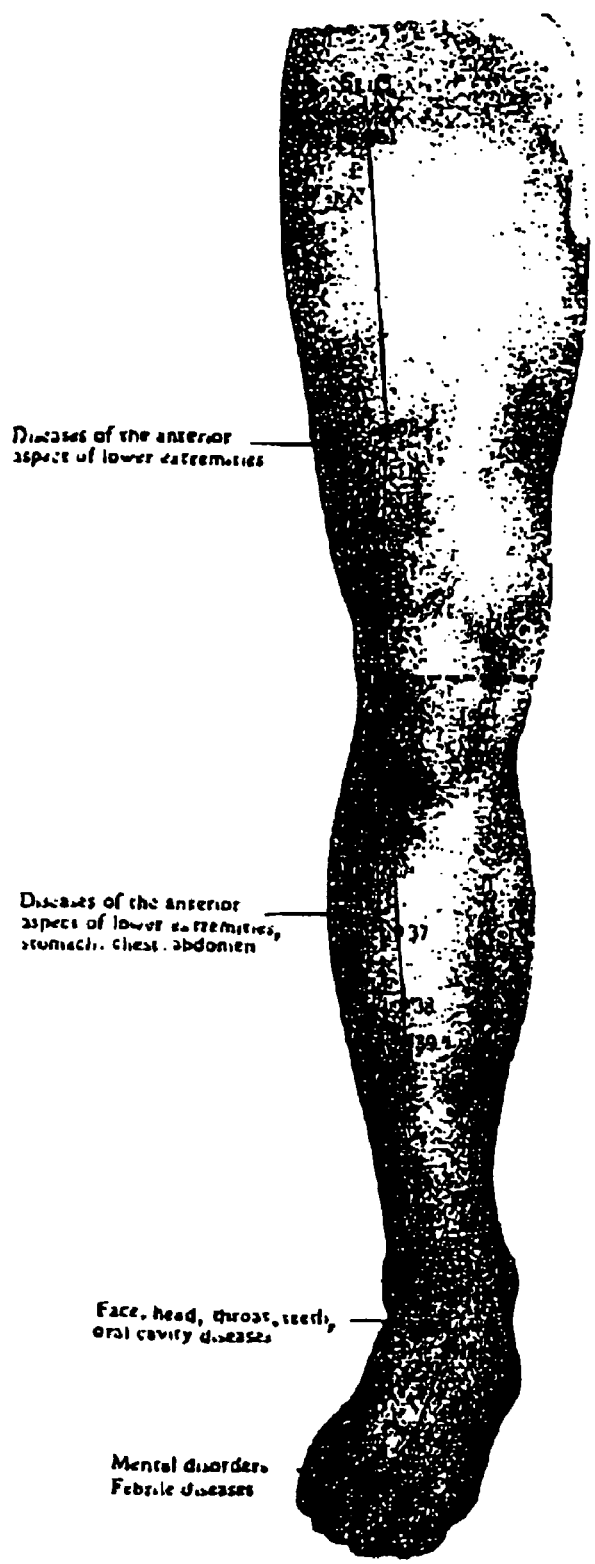
Figure 2D:
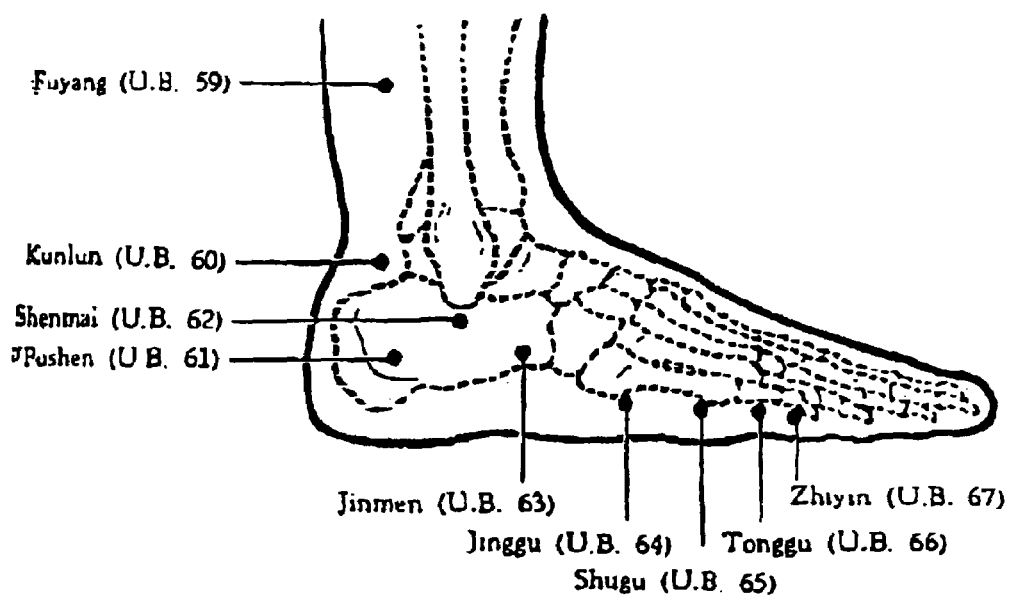
Figure 2E:
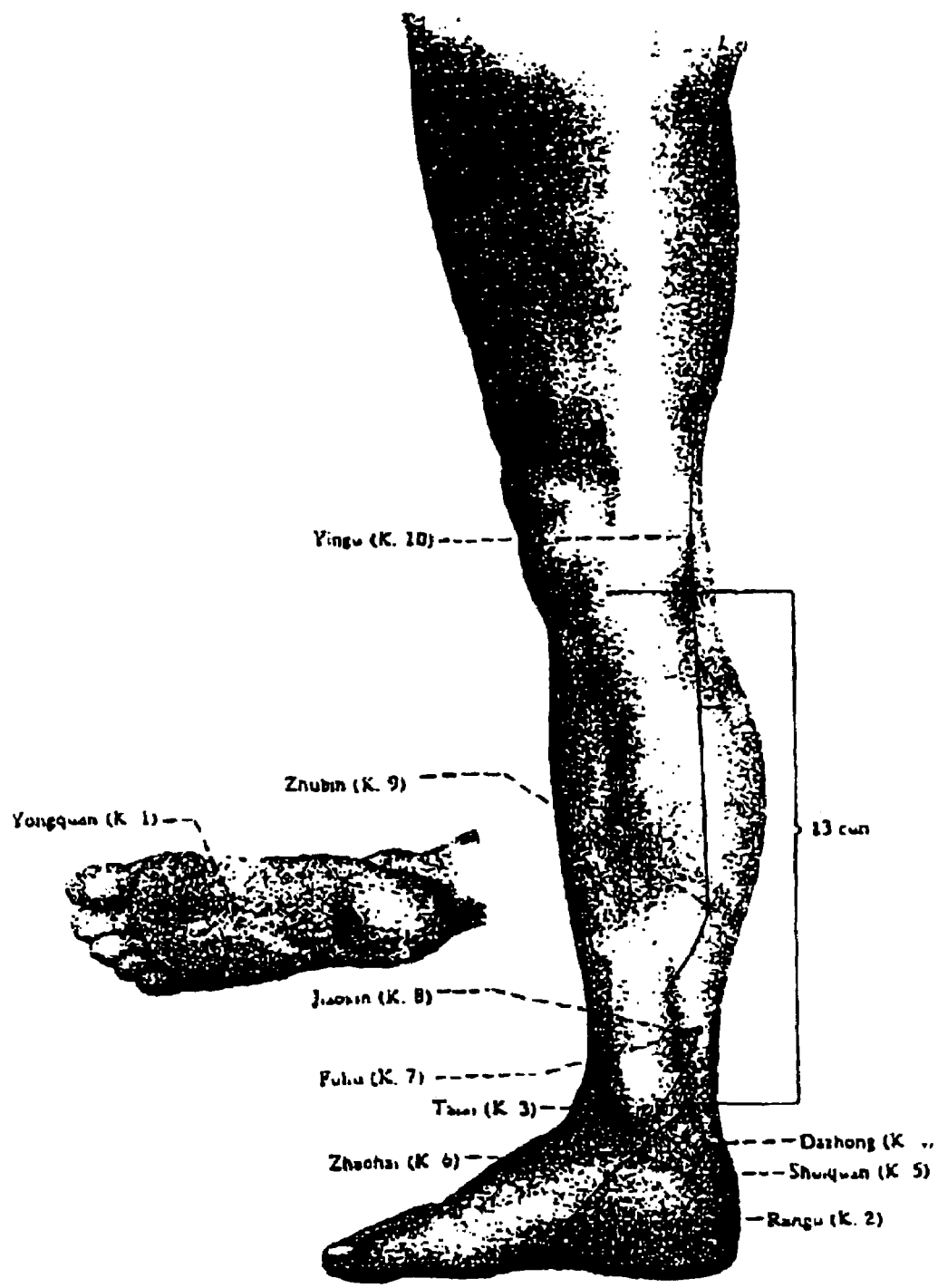
Figure 2F:
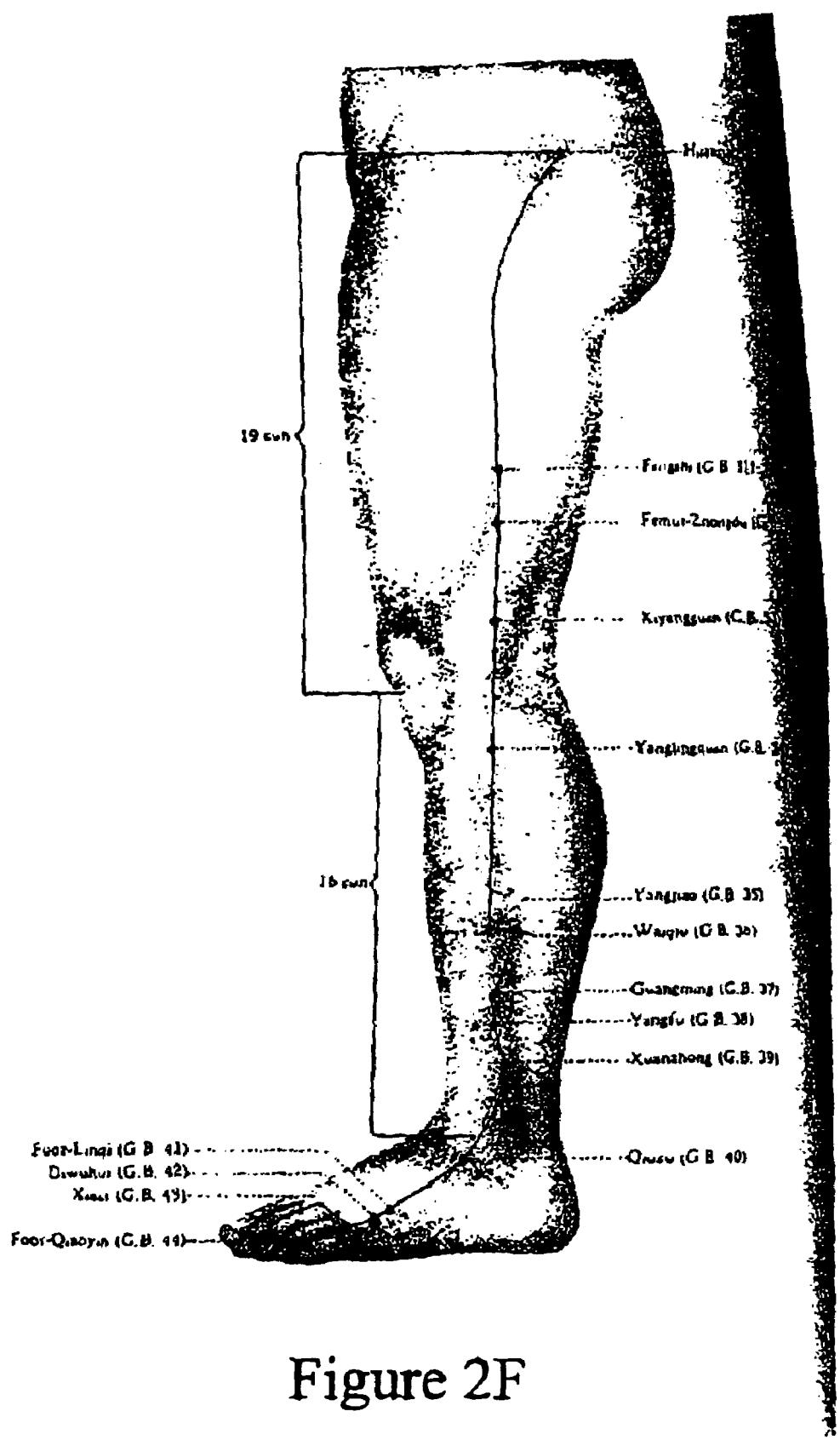
Figure 2G:
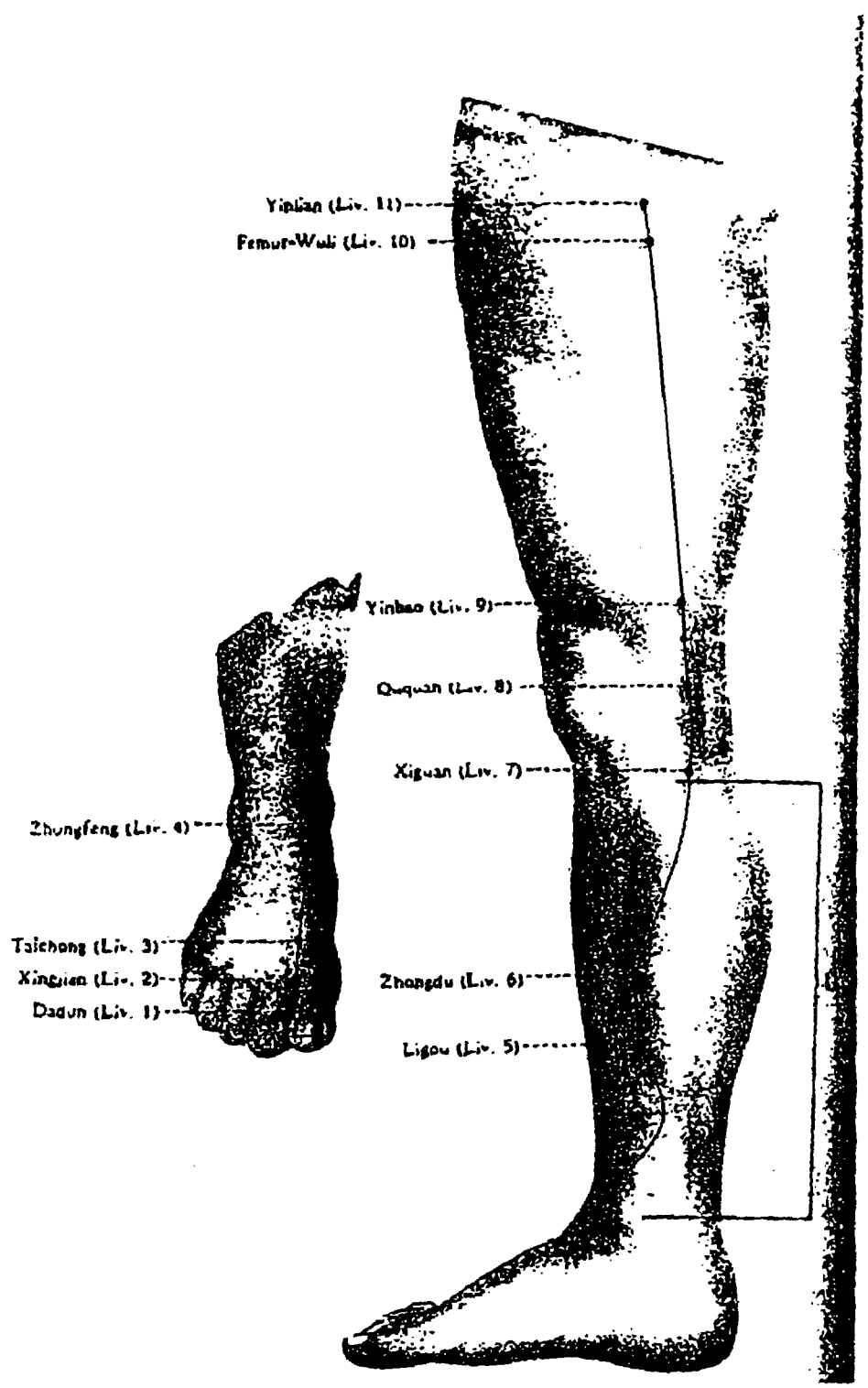

FIG. 1 illustrates the laser-ionization therapy system according to the principles of the present invention.

According to the principles of the present invention, the laser-ionization therapy system is capable of relaxing a patient's body at the cellular level to increase the efficiency at which toxins are removed from the body.

Referring to FIG. 1, the laser-ionization therapy system 100 may generally comprise an ion generating unit 200 and a cold laser unit 300.

In one aspect of the present invention, the ion generating unit 200 comprises a power supply 210, an electrode array 220 coupled to the power supply 210, and a reservoir 230. The electrode array 220 may be comprised of slow-corroding, replaceable electrodes mounted within a housing 224. The electrodes within the electrode array 220 may comprise an anode 226 and a cathode 228. The power supply 210 is capable of delivering a low voltage direct current to the electrode array 220 and may further comprise a display screen 212 (e.g., an LED display) capable of displaying the voltage and amperage of a treatment power applied from the power supply 210 to the electrode array 220. The display screen 212 may also be capable of displaying amount of time elapsed during treatment of a patient.

The power supply 210 may be programmed with at least five ionization treatment options: at least three ionization treatment options may be pre-programmed and at least two ionization treatment options may be custom designed for each patient. In one aspect of the present invention, the custom designed ionization treatment options may be designed based on results of a first muscle testing procedure.

In one aspect of the present invention, a first ionization treatment option may result in the generation of only positive ions within a predetermined treatment time (e.g., about 30 minutes). A second ionization treatment option may result in the generation of only negative ions within the predetermined treatment time. A third ionization treatment option may result in the generation of a mix of positive and negative ions such that about 70% of the generated ions are positive while about 30% of the generated ions are negative. A fourth ionization treatment option may result in the generation of positive ions for about 15 minutes, then negative ions for about 10 minutes, and finally positive ions for about 5 minutes. A fifth ionization treatment option may result in the generation of negative ions for about 15 minutes, then positive ions for about 10 minutes, and finally negative ions for about 5 minutes.

The cold laser unit 300 may, for example, comprise a base unit 310 and a probe 320 coupled to the base unit 310 via an optical cable 330. According to the principles of the present invention, substantially coherent light (e.g., laser light) may be generated by the base unit 310 and transmitted to the probe 320 via the optical cable 330. Light exiting the probe 320 may be directed toward predetermined areas of the patient's body. In one aspect of the present invention, the base unit 310 may generate light at a wavelength of substantially between about 630 and about 640 nm and at a power of about 5 Mw or less. In one aspect of the present invention, light generated by the base unit 310 has a wavelength of substantially about 635 nm. In one aspect of the present invention, generated light may be directed toward the patient's body as a substantially continuous beam of light or a pulsed beam having a predetermined frequency. In one aspect of the present invention, pulsing of the light directed toward the patient may alleviate pain and increase circulation within the body, stimulate glands, etc. In one aspect of the present invention, the frequency at which light directed toward the patient is pulsed may determined based on results of a second muscle testing procedure and the location of the patient's body where the light is to be directed.

According to the principles of the present invention, the electrode array 220 may be placed in the reservoir 230 and immersed in water 112 contained therein. In one aspect of the present invention, the water 112 may be provided as normal tap water. In another aspect of the present invention, a predetermined amount (e.g. a half cup) mineral salts and/or a predetermined amount (e.g., about 1 tsp) of liquid minerals may be mixed with the water 112 to enhance the electrical conductivity characteristics of the water 112. In one aspect of the present invention the liquid minerals may include magnesium with 50 types of trace minerals.

As mentioned above, the power supply 210 is capable of delivering a low voltage direct current to the electrode array 220. In one aspect of the present invention, the low voltage direct current has a current and voltage of about 2.45 Amps. and about 19 V, respectively. Upon receipt of the low voltage direct current at the electrode array 220, water 112 within the reservoir 230 may become oxidized (i.e., $2H_2O \rightarrow O_2+4H^++4e^-$)at the anode 226 while the water 112 may be reduced (i.e., $4H_2O+4e^- \rightarrow 2H_2+4OH^-$)at the cathode 228. When the low voltage direct current is positive, the ions generated in the water 112 will generally be negative in polarity. Alternatively, when the low voltage direct current is negative, the ions generated in the water 112 will generally be positive in polarity. By changing the polarity of the low voltage applied to the electrode array 220, the amount and polarity of ions generated within the water may be selectively adjusted. The generated ions permeate the patient's body and attach themselves to oppositely charged particles, thereby neutralizing toxins within the body. The neutralized toxins are then removed from the patient's body by a process known as dispersion. Substantially simultaneously with the generation of the ions, the base unit 310 may be activated such that light may be directed toward predetermined areas of the patient's body using the probe 320. In one aspect of the present invention, light generated by the base unit 310 may be emitted toward the patient's body during the entire time ions are generated by the ion generating unit 200.

In one aspect of the present invention, the reservoir 230 may be made of a transparent material, electrically insulative, and capable of holding water (e.g., plastic, glass, etc.). Accordingly, the probe 320 may be arranged proximate exterior of the reservoir 230 such that light emitted from the probe 320 is transmitted through the reservoir 230 and water 112 and onto predetermined areas of the patient's body that are in contact with the water 112. In another aspect of the present invention, the probe may be arranged proximate predetermined areas of the patient's body that are not in contact with the water 112 such that light emitted by the probe 320 directly irradiates the predetermined area of the patient's body.

During and after the laser-ionization treatment, the water 112 within the reservoir 230 may turn different colors and consistencies. The change in the water is the result of the toxins being extracted from the body as a result of the combined actions of the laser light and the generated ions. For example, the water 112 may turn yellow-green when it contains toxins extracted from the patient's kidney, bladder, urinary tract, and the prostate area. The water 112 may turn orange when it contains toxins extracted from the patient's joints. The water 112 may turn brown when it contains toxins extracted from the patient's liver. Brown colored water also contains tobacco and cellular debris. The water 112 may turn black when it contains toxins extracted from the patient's gallbladder and liver. The water 112 may turn dark green when it contains toxins extracted from the patient's gallbladder. The water 112 may turn white and foamy when it contains mucous extracted from the patient's lymphatic system. The water 112 may contain white cheese-like particles, indicating the presence of yeast. The water 112 may contain black flecks of material, indicating the presence of heavy metals. Lastly, the 112 may contain red flecks, indicating the presence of blood clot material. In some cases, parasites, pinworms, and pungent purple mucous may form within the water when the patient is on dairy allergy medication.

TABLE 1

| Analyte | Plain Tap Water (ppb) | Ion Generating Unit after 30 mins. (ppb) | Laser-Ionization Therapy System after 30 mins. (ppb) |
|---|---|---|---|
| Antimony | <1 | <1 | <1 |
| Cadmium | <0.3 | <0.3 | <0.3 |
| Chromium | 4.6 | 4000 | 8400 |
| Cobalt | <10 | 38 | 63 |
| Iron | 20 | 19,000 | 40,000 |

As shown above in Table 1, the amount of toxins (e.g., analyte) found in water 112 within reservoir 230, prior to performing any detoxification therapy, contains a base amount of toxins. After performing related art detoxification treatments, such as those including only the activation of devices similar to the ion generation unit 200 for about 30 minutes, water 112 within the reservoir 230 contained approximately three orders of magnitude more toxins than water obtained prior to the treatment. However, after performing the laser-ionization therapy in accordance with the principles of the present invention, water 112 within the reservoir 230 contained roughly double the amount of toxins found in the water after performing the related art therapy. Further, the laser-ionization therapy method and system removed roughly double the amount of toxins from the patient's body, as compared with results of the related art therapy, within substantially the same amount of time (about 30 minutes).

In one aspect of the present invention, and as already mentioned above, the appropriate mix and polarity of generated ions must be determined for each patient through a first muscle testing procedure. Further, the amount and type of ions generated may be based, at least in part, on the pH of the patient's saliva. For example, alkaline saliva generally corresponds to a first muscle testing procedure requiring the treatment involve the generation of predominantly positive ions. Alternatively, acidic saliva generally corresponds to a first muscle testing procedure requiring the treatment involve the generation of predominantly negative ions.

Also as mentioned above, the frequency at which light directed toward the predetermined area of the patient's body depends on the location of the predetermined area and a second muscle testing procedure. Below, Table 2 lists object of the therapeutic treatment (column A), the corresponding area of body involved with irradiation of the light generated by the base unit 310 (column B), and the corresponding pulse frequency of the light emitted by the probe 320, in pulses per second (column C). Depending upon the results of the second muscle testing procedure, light directed is pulsed at a predetermined frequency for different areas of a patient's body. Further, FIGS. 2A-2G illustrate meridian points that may be irradiated with light generated by the base unit 310.

TABLE 2

| A | B | C |
|---|---|---|
| Allergies | Lungs, Sinus | 1, 2, 4, 120, 213, 273, 500 |
| Adrenal | AOI (area of involvement) | 21, 24 |

TABLE 2-continued

| A | B | C |
|---|---|---|
| Anemia | Navel, Spleen, Sternum | 2, 10, 50, 260 |
| Arthritis | AOI | 10, 20, 25, 48, 50 |
| Asthma | Lungs, T-1 to T-4 | 2, 41, 120, 213, 273 |
| Backache | AOI | 5, 6, 7, 72, 100 |
| Bacteria | AOI, Thymus, Spleen | 1, 3, 5, 6, 83, 100, 187, 351 |
| Bacterial Virus | AOI | 6, 84 |
| Bowel Flora | AOI, Bowel | 2, 21, 24, 250 |
| Brain | Brain, Cerebellum | 8, 13, 15, 33, 37, 60, 61 |
| Brain Stem | Brain Stem | 2, 210 |
| Bruises | AOI | 5, 10, 12, 50 |
| Burns | AOI, Lymphatics | 10, 17, 20, 25, 30, 50 |
| Circulation | AOI | 8, 11, 16, 31, 46, 633 |
| Prostate | Prostate | 15, 16, 31, 33 |
| Red Blood Cells | AOI | 11, 45 |
| Scar Tissue | AOI | 18, 20, 25, 279 |
| Sinuses | AOI | 2, 4, 6, 86, 120, 323 |
| Skin Rash | AOI, Liver | 1, 363 |
| Sore Throat | AOI | 5, 9, 12, 42, 53, 91 |
| Stroke | AOI, Brain | 2, 310 |
| Testosterone | AOI | 4, 141 |
| Thymus | Thymus | 3, 11, 20, 25, 45, 153 |
| Ulcers | AOI, Nerve Root | 4, 22, 23, 133 |
| Warts | AOI, Liver | 10, 52 |
| Wrinkles | AOI | 1, 363 |
| Yeast | AOI, Yeast Point | 6, 12, 41, 77 |
| Colic & Colitis | AOI, T-5, L-5 | 200 |
| Constipation | G.I. T-8 to Sacrum | 1, 3, 17, 19, 26, 29, 200, 343 |
| Cramps | G.I. T-10 to L-5 | 1, 9, 10, 50, 53, 373 |
| Depression | Brain | 3, 14, 37, 180 |
| Diabetic Ulcers | AOI, Nerve Root | 1, 22, 23, 633 |
| Earaches | AOI, Lymphatics | 5, 100 |
| Eczema | AOI, Liver | 1, 2, 15, 33, 339, 353 |
| Emotion | AOI, Organ | 16, 31 |
| Fractures, Bones | AOI, Nerve Root | 8, 9, 11, 15, 20, 25, 33, 45, 65, 562 |
| Frozen Shoulder | AOI, Nerve Root | 5, 9, 10, 13, 40, 50, 56, 107 |
| Fungus | AOI | 9, 53 |
| Gallbladder | Gallbladder | 1, 9, 13, 38, 55, 458 |
| Gums | AOI | 5, 6, 83, 104 |
| Hearts | Heart | 8, 15, 33, 60 |
| Hip Pain | Hip, Nerve Root | 7, 9, 56, 75 |
| Inflammation | AOI, Lymphatics | 2, 20, 25, 300 |
| Kidney | Kidney | 1, 12, 43, 430 |
| Liver | Liver | 9, 53 |
| Liver Spots | AOI, Liver | 13, 38 |
| Lymes | AOI, Thymus, Liver, Kidney | 2, 242, 327, 654, 655, 763, 764 |
| Lymphatics | Lymphatic system | 2, 4, 12, 20, 25, 42, 139, 300 |
| Macrophages | AOI | 6, 84 |
| Muscle Pain | AOI, Nerve Root | 2, 9, 12, 42, 56, 313 |
| Nausea | Stomach, Over Lip | 1, 12, 14, 37, 42, 825 |
| Neck Pain | AOI | 9, 10, 13, 40, 50, 56 |
| Nerve | AOI, Nerve Root | 1, 8, 60, 61, 338, 463 |
| Pain | AOI, Nerve Root, Brain | 2, 9, 10, 12, 13, 15, 40, 42, 50, 56, 313 |
| Parasites | AOI | 3, 5, 6, 7, 10, 50, 71, 83, 100, 167, 650, 655, 764, 769 |

In accordance with the principles and results of the present invention, there are many possible devices to implement the present invention. As an example, the ion generating unit 200 may be embodied as a device commonly known as Ion Cleanse™, manufactured by Stargate International (at 10235 S. Progressive Way, #7, Parker Colorado, 80134), the cold laser unit 300 may be embodied as a device commonly known as Erchonia Laser PL4™, manufactured by Erchonia (at 3960 E. Palm Lane, #9, Mesa, Ariz., 85296), and the liquid minerals may be embodied as liquid minerals commonly known as Thor Liquid Ionic Minerals™, manufactured by Thor, Inc. (at Ogden, Utah, 84401).

In accordance with the principles of the present invention, sore muscles, high blood pressure, swelling in joints, arthritis, sever stress, pain, ADD, ADHD, pain, toxemia, and the like may be alleviated using the system and method described above.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A laser ionization detoxification therapy system, comprising:
    a reservoir that holds water;
    an ion generating unit that includes an electrode array in the reservoir that generates ions in the water, wherein the water with the ions is capable of receiving a therapy subject; and
    a cold laser unit that produces substantially coherent light that is capable of being irradiated onto the therapy subject,
    wherein the ion generating unit alternately produces positive ions and negative ions.

2. The system of claim 1, wherein the reservoir is transparent.

3. The system of claim 1, wherein the ion generating unit further includes a power supply.

4. The system of claim 3, wherein the power supply provides a direct current to the electrode array.

5. The system of claim 4, wherein the direct current has a current of about 2.45 amps.

6. The system of claim 4, wherein the power supply unit further includes a display screen that displays the voltage and amperage provided by the power supply to the electrode array.

7. The system of claim 1, wherein the electrode array includes corrosion resistant, replaceable electrodes.

8. The system of claim 7, wherein the electrode array further includes an anode and cathode.

9. The system of claim 1, wherein the cold laser unit further includes:
    a base unit that generates the substantially coherent laser light;
    an optical cable connected to the base unit; and
    a probe connected to the optical cable,
    wherein the laser light is transmitted from the base unit to the probe via the optical cable and the laser light is emitted from the probe.

10. The system of claim 1, wherein the laser light has a wavelength between about 630 nm and 640 nm.

11. The system of claim 10, wherein the laser light has a power of less than about 5 mW.

12. The system of claim 1, wherein the wavelength of the laser light is about 635 nm.

13. The system of claim 1, wherein the laser light is substantially continuous.

14. The system of claim 1, wherein the laser light is pulsed.

15. The system of claim 1, wherein the laser light is pulsed and has a wavelength between about 630 nm and 640 nm and a power of less than about 5 mW.

16. The system of claim 1, wherein:
    the ion generating unit further includes a power supply that provides a direct current to the electrode array,
    the electrode array includes corrosion resistant, replaceable electrodes, and
    the electrode array further includes an anode and cathode.

17. A laser ionization detoxification therapy system, comprising:
    a reservoir that holds water;
    an ion generating unit that includes an electrode array in the reservoir that generates ions in the water, wherein the water with the ions is capable of receiving a therapy subject; and
    a cold laser unit that produces substantially coherent light that is capable of being irradiated onto the therapy subject,
    wherein the laser light has a wavelength between about 630 nm and 640 nm, and
    wherein the ion generating unit produces positive ions.

18. A laser ionization detoxification therapy system, comprising:
    a reservoir that holds water;
    an ion generating unit that includes an electrode array in the reservoir that generates ions in the water, wherein the water with the ions is capable of receiving a therapy subject; and
    a cold laser unit that produces substantially coherent light that is capable of being irradiated onto the therapy subject,
    wherein the laser light has a wavelength between about 630 nm and 640 nm, and
    wherein the ion generating unit produces negative ions.

* * * * *